US009682106B2

(12) United States Patent
Kasahara et al.

(10) Patent No.: US 9,682,106 B2
(45) Date of Patent: *Jun. 20, 2017

(54) METHOD FOR COMBINED CONDITIONING AND CHEMOSELECTION IN A SINGLE CYCLE

(71) Applicant: THE REGENTS OF THE UNIVERSITY OF CALIFORNIA, Oakland, CA (US)

(72) Inventors: Noriyuki Kasahara, Miami, FL (US); Robert H. Schiestl, Encino, CA (US); Katrin Hacke, Los Angeles, CA (US); Akos Szakmary, Vienna (AT); Gay M. Crooks, Sherman Oaks, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,776

(22) Filed: May 16, 2016

(65) Prior Publication Data

US 2016/0256494 A1 Sep. 8, 2016

Related U.S. Application Data

(63) Continuation of application No. 14/112,878, filed as application No. PCT/US2012/034586 on Apr. 20, 2012, now Pat. No. 9,439,928.

(60) Provisional application No. 61/477,440, filed on Apr. 20, 2011.

(51) Int. Cl.
*A61K 35/28* (2015.01)
*A61K 31/52* (2006.01)
*A61K 31/7076* (2006.01)
*C12N 5/10* (2006.01)
*C12N 5/0789* (2010.01)
*A61K 35/12* (2015.01)

(52) U.S. Cl.
CPC .............. *A61K 35/28* (2013.01); *A61K 31/52* (2013.01); *A61K 2035/124* (2013.01)

(58) Field of Classification Search
CPC .... A61K 35/28; A61K 31/52; A61K 31/7076; C12N 5/0647; C12N 5/10
USPC .............. 424/93.21, 93.7; 536/22.1; 435/455
See application file for complete search history.

(56) References Cited

U.S. PATENT DOCUMENTS

| 7,094,885 B2 | 8/2006 | Fritzberg |
| 9,439,928 B2* | 9/2016 | Kasahara ............... A61K 35/14 |
| 2003/0032003 A1* | 2/2003 | Schiestl ............ A01K 67/0271 435/5 |
| 2003/0073649 A1 | 4/2003 | DiMartino et al. |

FOREIGN PATENT DOCUMENTS

| WO | WO9819540 A1 | 5/1997 |
| WO | WO9735477 A1 | 10/1997 |
| WO | WO9743900 A1 | 11/1997 |
| WO | WO9925367 A2 | 5/1999 |
| WO | WO0240049 A2 | 5/2002 |

OTHER PUBLICATIONS

Aubrecht, J. et al., "Tissue Specific Toxicities of the Anticancer Drug 6-Thioguanine Is Dependent on the Hprt Status in Transgenic Mice", J. Pharm. Exp. Ther. 1997, 282(2):1102-1108.
Bhattacharya, D. et al., "Space-time considerations for hematopoietic stem cell transplantation", Eur. J. Immunol., 2008, 38(8):2060-2067.
Delicou, S. et al., "Successful HLA-identical hematopoietic stem cell transplantation in a patient with purine nucleoside phosphorylase deficiency", Pediatric Transplantation, 2007, 11:799-803.
Foss, F. M. et al., "The Role of Purine Analogues in Low-Intensity Regimens With Allogeneic Hematopoietic Stem Cell Transplantation", Semin. Hematol., 2006, 43(suppl 2):S35-S43.
Giralt, Sergio, et al., "Engraftment of Allogenic Hematopoietic Progenitor Cells With Purine Analog-Containing Chemotherapy: Harnessing Graft-Versus-Leukemia Without Myeloablative Therapy", Jun. 15, 1997, pp. 4531-4536, XP002101604, vol. 89, No. 12, Publisher: Blood, American Society of Hematology, Published in: United States.
Hacke, K., "Combined preconditioning and in vivo chemoselection with 6-thioguanine alone achieves highly efficient reconstitution of normal hematopoiesis with HPRT-deficient bone marrow", Exp. Hematol., 2012, 403: 3-13.
Neff, T.. et al., "Survival of the fittest: in vivo selection and stem cell gene therapy", Blood, 2006, 107:1751-1760.
Porter, C. C.. et al., "Interfering RNA-mediated purine analog resistance for in vitro and in vivo cell selection", Blood, 2008, 112(12):4466-4474.
International Search Report & Written Opinion, PCT/US2012/034586, Jul. 3, 2012.
Extended European Search Report in corresponding European Application 12774246.8, Oct. 20, 2014, Published in: European Patent Office.
Office Action dated Mar. 22, 2016 from corresponding Russian Federation Application No. 2013151632, filed Apr. 20, 2012 (WO2012145723).

(Continued)

*Primary Examiner* — Anne Marie S Wehbe
(74) *Attorney, Agent, or Firm* — Karen S Canady; canady + lortz LLP (57) ABSTRACT

A method of radiation-free hematopoietic stem cell (HSC) transplantation comprises administering to a mammalian subject one or two doses of 2 to 10 mg/kg body weight of a purine base analog, such as 6TG as a pre-conditioning step. The method further comprises engrafting into the subject hypoxanthine-guanine phosphoribosyltransferase (HPRT)-deficient donor HSCs within 48 to 72 hours of the pre-conditioning step; and administering to the subject about 1 to 5 mg/kg of the purine base analog every two to four days for two to eight weeks following the engrafting step. The method is performed in the absence of pre-conditioning via radiation. The subject is therefore not treated with myeloablative radiation in preparation for transplantation, and thus the subject is free of myeloablative radiation-induced toxicity.

44 Claims, 6 Drawing Sheets

(56) References Cited

OTHER PUBLICATIONS

English Translation of Office Action dated Mar. 22, 2016 from corresponding Russian Federation Application No. 2013151632, filed Apr. 20, 2012 (WO2012145723).

* cited by examiner

METHOD FOR COMBINED CONDITIONING AND CHEMOSELECTION IN A SINGLE CYCLE

This application claims the benefit of U.S. provisional patent application No. 61/477,440, filed Apr. 20, 2011, the entire contents of each of which are incorporated herein by reference. Throughout this application various publications are referenced. The disclosures of these publications in their entireties are hereby incorporated by reference into this application in order to describe more fully the state of the art to which this invention pertains.

STATEMENT REGARDING FEDERALLY SPONSORED RESEARCH

This invention was made with Government support of Grant No. AI067769, awarded by the National Institutes of Health. The Government has certain rights in the invention.

BACKGROUND

Hematopoietic stem cell transplantation (HSCT) is a mainstay of treatment for many hereditary disorders and lymphohematopoietic malignancies (1). Furthermore, hematopoietic stem cells (HSC) in general represent an important target for ex vivo gene therapy. Gene transfer into HSC provides a potential strategy for both correcting monogenic defects and altering drug sensitivity of normal BM to cytotoxic drugs. These applications have significant therapeutic potential but have been limited by low gene transfer into HSC. Recent advances, such as improved cytokines for minimizing commitment during ex vivo manipulation, fibronectin-assisted gene transfer and enrichment of HSC prior gene transfer have improved the efficiency of gene transfer into human cells and enhanced human gene therapy trials (2). However, the efficiency of gene transfer into HSC and the engraftment of large numbers of transduced cells remains a major challenge to broaden the application of this technology for the successful treatment of cancer and monogenetic diseases.

In order to enhance engraftment of gene-modified HSC and to decrease the time needed for lymphohematopoietic reconstitution after HSCT, in vivo selection strategies employing drug resistance genes such as dihydrofolate reductase (DHFR) (3) or multiple drug-resistance gene 1 (MDR1) (4, US1996/017660) have been tested but have generally failed due to unacceptable toxicity (5) or insufficient selection efficiency (6). Currently, mutant forms of O6-methylguanine-DNA-methyltransferase (MGMT) are being tested for their ability to confer chemoprotection against BCNU or temozolomide in combination with O6-benzylguanine (2,7, US1997/004917), but these agents pose a considerable risk of toxicity, and recent observations suggest that mutant MGMT may confer a selective disadvantage when expressed at high levels (8). In US2003032003AA a selection strategy has been described for selecting HPRT-deficient cells in vivo by 6TG. However, in this patent application either irradiation is still used for preconditioning prior in vivo selection or in vivo selection is performed in cycles with recovery periods in between 6TG administration.

Furthermore, the suggested 6TG dose is high and administrated over a long time period (200 mg/kg total dose over 55 days). In addition, an approach to inactivate HPRT expression in BM and subsequently select the donor cells with 6TG in vivo has been reported by Porter and DiGregori as "interfering RNA mediated purine analog resistance" ('iPAR'). This report demonstrated the feasibility of HPRT inactivation in HSC with a lentiviral vector expressing shRNA targeting Hprt and enrichment for these altered hematopoietic cells with 6TG in mice in vivo. However, in this report, pre-conditioning was still performed by total body irradiation, and in vivo chemoselection was not initiated until at least 4 weeks post-transplant. In addition, 6TG was administered either as a short pulse or at dosages chosen to be only moderately myelosuppressive, and it is not clear whether adequate levels of HSC transduction were achieved by the second-generation lentiviral vectors employed in their study. Overall, the engraftment levels reported were variable and relatively modest. There remains a need for more effective methods of HSCT that avoid toxicity while reconstituting bone marrow cells.

REFERENCES (1) Bhattacharya D, Ehrlich L I, Weissman I L. EurJ Immunol. 2008; 38:2060-2067.
(2) Milsom M D, Williams D A. DNA Repair (Amst). 2007; 6:1210-1221.
(3) Williams D A, Hsieh K, DeSilva A, Mulligan R C. J Exp Med. 1987; 166:210-218.
(4) Sorrentino B P, Brandt S J, Bodine D, et al. Science. 1992; 257:99-103.
(5) Zaboikin M, Srinivasakumar N, Schuening F. Cancer Gene Ther. 2006; 13:335-345.
(6) Southgate T, Fairbairn L J. Expert Rev Mol Med. 2004; 6:1-24.
(7) Neff T, Beard B C, Kiem H P. Blood. 2006; 107:1751-1760.
(8) Schambach A, Baum C. DNA Repair (Amst). 2007; 6:1187-1196.
(9) Porter C C, DeGregori J. Blood. 2008; 112:4466-4474.
In vivo selection of primitive hematopoietic cells (Patent pubication WO/1998/019540) US1996/017660
Use of mutant alkyltransferases for gene therapy to protect from toxicity of therapeutic alkylating agents (Patent publication WO/1997/035477) US1997/004917
In vivo selection (Patent publication WO/1997/043900) US2003032003AA

SUMMARY

The invention provides a method of radiation-free hematopoietic stem cell (HSC) transplantation. Typically, the method comprises administering to a mammalian subject one or two doses of 2 to 10 mg/kg body weight of a purine base analog as a pre-conditioning step. The method further comprises engrafting into the subject hypoxanthine-guanine phosphoribosyltransferase (HPRT)-deficient donor HSCs within 48 to 72 hours of the pre-conditioning step; and administering to the subject about 1 to 5 mg/kg of the purine base analog every two to four days for two to eight weeks following the engrafting step. The method is performed in the absence of pre-conditioning via radiation. The subject is therefore not treated with myeloablative radiation in preparation for transplantation, and thus the subject is free of myeloablative radiation-induced toxicity.

Representative examples of the purine base analog include: 6-thioguanine (6TG), 6-mercaptopurine (6-MP), and azathiopurine (AZA). In one embodiment, the purine base analog is 6TG. In some embodiments, the total 6TG dosage administered to the subject does not exceed 105 mg; typically, the total 6TG dosage administered to the subject does not exceed 75 mg. In one embodiment, the administering of purine base analog is performed every 3 days and for not more than four weeks following the engrafting step.

Subjects treated in accordance with the method will exhibit over 75% genetically modified hematopoietic cells. In some embodiments, the subject exhibits over 95% genetically modified hematopoietic cells.

The HPRT-deficient HSCs to be transplanted can be rendered HPRT-deficient using conventional methods known to those skilled in the art. Representative methods include, but are not limited to, introduction of sequences encoding zinc finger nucleases (ZFNs), transcriptional activator-like effector nucleases (TALENs), small fragment homologous recombination (SFHR) template strands, inhibitory RNAs (siRNAs) or microRNAs (miRNAs), antisense RNAs, trans-splicing RNAs, ribozymes, intracellular antibodies, or dominant-negative or competitive inhibitor proteins. The transplanted HSCs can be autologous, syngeneic, or allogeneic.

In some embodiments, the HPRT-deficient HSCs to be transplanted have been genetically modified. The subject may have a hereditary or genetic disorder, an acquired disease affecting lymphohematopoietic cells, such as human immunodeficiency virus (HIV) infection or acquired immune deficiency syndrome (AIDS), or a lymphohematopoietic malignancy. The genetic modification of the donor HSCs can extend beyond rendering the cells HPRT-deficient, and also serve to treat or correct a condition.

BRIEF DESCRIPTION OF THE FIGURES

FIG. 1A-1B. Optimization of 6TG conditioning regimen.

FIG. 2A-2B. Lack of progressive myelotoxicity after injection with conditioning doses of 6TG in HPRT-deficient mice, and low engraftment rate with 6TG conditioning alone. (FIG. 2A) HPRT-wt and HPRT-deficient mice were injected i.p. with 10 mg/kg 6TG on Days 1 and 3. On Day 7 after the first 6TG dose, paraformaldehyde-fixed bone sections were stained with H&E, and BM histology was examined. Representative photomicrographs (40× magnification) are shown.

FIG. 4A-4B. Optimization of combined 6TG conditioning and in vivo chemoselection strategy. Treatment schedule: HPRT-wt female recipient mice received the first conditioning dose of 6TG (10 mg/kg, i.p.) on Day-2, then were transplanted with HPRT-deficient male BM along with a second conditioning dose of 6TG (10 mg/kg, i.p.) on Day 0. In vivo chemoselection was then performed with repeated i.p. injections of 2.5 mg/kg or 5.0 mg/kg 6TG every 3 days for a period of 2 weeks (FIG. 4A) or 4 weeks (FIG. 4B), as indicated. Representative photomicrographs of bone marrow from paraformaldehyde-fixed sections stained with H&E (40× original magnification) are shown.

DETAILED DESCRIPTION

The invention provides a novel in vivo chemoselection strategy that exploits the essential role of hypoxanthine-guanine phosphoribosyltransferase (HPRT)-mediated conversion of 6-thioguanine (6TG) to thioguanine nucleotide in 6TG myelotoxicity. Because HPRT-deficiency per se does not impair hematopoietic cell development or function, it can be removed from hematopoietic cells to be used for transplantation. The in vivo chemoselection strategy involves HSCT performed with HPRT-deficient donor HSCs using 6TG both for myeloablative conditioning of HPRT-wild type recipients and for a single cycle in vivo chemoselection process of donor cells. The invention is based on the development and discovery of a dosing schedule at which 6TG induces selective myeloablation without any adverse effects on extra-hematopoietic tissues, while engrafted HSC deficient in HPRT activity are highly resistant to the cytotoxic effects of 6TG. With this strategy of combined 6TG conditioning and chemoselection, efficient and high engraftment of HPRT-deficient donor HSC with low overall toxicity can be achieved. 6TG in vivo chemoselection allows long-term reconstitution of immunophenotypically normal bone marrow (BM) by amplifying the self-renewing, pluripotent HSC population from HPRT-deficient donor (or engrafted) BM.

The method described herein for highly efficient and overall non-toxic conditioning and single cycle in vivo chemoselection is generally applicable as a strategy to improve HSCT engraftment efficiency and transplantation outcome, and to confer a selective advantage to genetically modified cells after ex vivo gene therapy. The in vivo chemoselection strategy exclusively employs 6TG, or other purine base analog, for both pre-conditioning and single cycle chemoselection of HPRT-deficient donor HSC, and is capable of achieving highly efficient engraftment and long-term reconstitution, with replacement of >95% of the recipient BM. This strategy is applicable for improving the engraftment of large numbers of ex vivo manipulated HSC to broaden the application of gene therapy in general.

DEFINITIONS

All scientific and technical terms used in this application have meanings commonly used in the art unless otherwise specified. As used in this application, the following words or phrases have the meanings specified.

As used herein, "radiation-free hematopoietic stem cell (HSC) transplantation" means that the recipient is not subjected to myeloablative conditioning via radiation. Instead, conditioning is achieved through administration of 6TG, typically administered during the 48 hours prior to (and including the day of) engraftment with donor HSCs.

As used herein, "HPRT-deficient" includes both cells that are naturally HPRT-deficient, and those rendered HPRT-deficient through genetic modification.

As used herein, "donor HSCs" or "donor cells" refers to the cells to be engrafted, regardless of whether the HSCs are derived from the recipient of the transplant or another subject. Thus, cells harvested from a subject can be modified and engrafted back into the same subject, becoming "donor cells". These may be referred to herein as "donor cells", "engrafted cells" or "transplanted cells".

As used herein, "a" or an means at least one, unless clearly indicated otherwise.

Combined Conditioning and Chemoselection for Hematopoietic Transplantation

The invention provides a method of radiation-free hematopoietic stem cell (HSC) transplantation. Typically, the method comprises administering to a mammalian subject one or two doses of 2 to 10 mg/kg body weight of a purine base analog as a pre-conditioning step. The method further comprises engrafting into the subject hypoxanthine-guanine phosphoribosyltransferase (HPRT)-deficient donor HSCs within 48 to 72 hours of the pre-conditioning step; and administering to the subject about 1 to 5 mg/kg of the purine base analog every two to four days for two to eight weeks following the engrafting step.

The method is performed in the absence of pre-conditioning via radiation. The subject is therefore not treated with myeloablative radiation in preparation for transplantation, and thus the subject is free of myeloablative radiation-induced toxicity. The method is contemplated for use with a variety of subjects, including subjects who have never received radiation treatment of any kind, subjects who have never received myeloablative radiation treatment, and subjects who have received myeloablative treatment in the past, but not within a time frame and/or at a dose that would be pre-conditioning for the method described herein. For example, the subject typically would not have received myeloablative radiation within 2 weeks, or even within 8 weeks, of the combined conditioning and chemoselection method described herein.

Representative examples of the purine base analog include: 6-thioguanine (6TG), 6-mercaptopurine (6-MP), and azathiopurine (AZA). In one embodiment, the purine base analog is 6TG. In some embodiments, the total 6TG dosage administered to the subject does not exceed 105 mg; typically, the total 6TG dosage administered to the subject does not exceed 75 mg. In one embodiment, the administering of purine base analog is performed every 3 days and for not more than four weeks following the engrafting step.

Where an alternative to 6TG is used as the purine base analog, known online (e.g., rxlist.com) and other resources are available to guide the skilled clinician in identifying a suitable dose for use in the method of the invention. For example, the usual oral dose for 6TG single-agent chemotherapy in pediatric patients and adults is 2 mg/kg of body weight per day; if no treatment response is observed after 4 weeks, the dose can be increased to 3 mg/kg. As much as 35 mg/kg has been given in a single oral dose with reversible myelosuppression observed.

For acute lymphatic leukemia, the usual initial dosage for pediatric patients and adults is 2.5 mg/kg 6-MP of body weight per day (100 to 200 mg in the average adult and 50 mg in an average 5-year-old child). Pediatric patients with acute leukemia have tolerated this dose without difficulty in most cases; it may be continued daily for several weeks or more in some patients. If, after 4 weeks at this dosage, there is no clinical improvement and no definite evidence of leukocyte or platelet depression, the dosage may be increased up to 5 mg/kg daily. A dosage of 2.5 mg/kg/day may result in a rapid fall in leukocyte count within 1 to 2 weeks in some adults with acute lymphatic leukemia and high total leukocyte counts. Once a complete hematologic remission is obtained, maintenance therapy is considered essential. Maintenance doses will vary from patient to patient. The usual daily maintenance dose of 6-MP is 1.5 to 2.5 mg/kg/day as a single dose.

Dosage for 6-TG and 6-MP is somewhat comparable, while dosage for AZA is more difficult to compare, because it needs first to be bioactivated to 6-MP, and it is usually not used for treating leukemia. For patients receiving solid organ transplantation, the dose of AZA required to prevent rejection and minimize toxicity will vary with individual patients, necessitating careful management. The initial dose is usually 3 to 5 mg/kg daily, beginning at the time of transplant. AZA is usually given as a single daily dose on the day of, and in a minority of cases 1 to 3 days before, transplantation. Dose reduction to maintenance levels of 1 to 3 mg/kg daily is usually possible. The dose of AZA should not be increased to toxic levels because of threatened rejection.

The HPRT-deficient donor HSCs can be naturally HPRT-deficient, or rendered HPRT-deficient through genetic modification. In this context, "donor HSCs" refers to the cells to be engrafted, regardless of whether the HSCs are derived from the recipient of the transplant or another subject. The transplanted HSCs can be autologous, syngeneic, or allogeneic.

The genetic modification can be achieved using any of a variety of means known to those skilled in the art. Examples of suitable means of genetic modification include, but are not limited to, introduction of sequences encoding zinc finger nucleases (ZFNs), transcriptional activator-like effector nucleases (TALENs), small fragment homologous recombination (SFHR) template strands, inhibitory RNAs (siRNAs) or microRNAs (miRNAs), antisense RNAs, trans-splicing RNAs, ribozymes, intracellular antibodies, or dominant-negative or competitive inhibitor proteins. The modification can be employed directly with the donor HSCs or with progenitors. These technologies can be used for genetic modification of a variety of cell types, including but not limited to hematopoietic progenitor cells or hematopoietic stem cells directly, as well as other types of adult or embryonic stem cells or induced pluripotent stem cells that can be differentiated or trans-differentiated into hematopoietic progenitor or hematopoietic stem cells.

In some embodiments, the HPRT-deficient HSCs to be transplanted have been genetically modified to suit a particular therapeutic objective. For example, the donor HSCs can be modified to correct a hereditary genetic defect, to alter drug sensitivity of normal bone marrow to cytotoxic drugs, to confer resistance to infectious microorganisms that affect lymphohematopoietic cells, to replace or re-set the endogenous immune system, or to combat lymphohematopoietic malignancies through replacement of endogenous bone marrow and induction of a graft-vs.-leukemia/lymphoma effect.

More specifically, hereditary genetic defects can include, but are not limited to, disorders of hematopoiesis including hemoglobinopathies such as sickle cell anemia, thalassemia, hereditary spherocytosis, G6PD deficiency, etc., disorders of immunologic or antimicrobial function such as severe combined immunodeficiency (SCID), chronic granulomatous disease (CGD), disorders of thrombopoiesis leading to coagulation defects such as Wiscott-Aldrich syndrome (WAS), as well as other genetic structural or metabolic disorders which can be ameliorated by genetic engineering of hematopoietic cells that travel to sites of tissue damage, such as various forms of epidermolysis bullosa (EB), and mucopolysaccharidosis.

Diseases in which modification of the drug sensitivity of bone marrow to chemotoxic drugs would be advantageous include, but are not limited to, malignant diseases that are treated by chemotherapy agents whose maximum tolerated dosage is limited by myelotoxicity. These include lung cancer, colorectal cancer, breast cancer, prostate cancer, pancreatic cancer, gastric cancer, liver cancer, head and neck cancer, renal cell carcinoma, bladder cancer, cervical cancer, ovarian cancer, skin cancer, sarcomas, and glioma.

Diseases in which bone marrow or hematopoietic stem cell transplantation is used to replace or reset the endogenous immune system include, but are not limited to, inflammatory bowel disease, scleroderma, and lupus erythematosis.

Diseases in which conferring resistance to infectious microorganisms would be advantageous include, but are not limited to, HIV infection and AIDS, HTLV infection, and parvovirus B19 infection.

Malignant or pre-malignant diseases of lymphohematopoiesis that are treated by bone marrow or hematopoietic stem cell transplantation include, but are not limited to, acute myelogenous leukemia, acute lymphocytic leukemia, lymphoma, and myelodysplastic syndromes.

Another example of the therapeutic application of this technology would be to improve the outcome of bone marrow or hematopoietic stem cell transplantation after acquired injury to endogenous lymphohematopoiesis caused by radiation injury, and chemotoxins.

A non-therapeutic but commercially useful application of this technology would be its use to generate humanized animal models, in which their endogenous lymphohematopoiesis is almost entirely replaced by cells from a human donor. Once generated, such animals could be used, for example, to test the myelotoxicity of new drugs being considered for application to human disease. This is advantageous because the sensitivity of hematopoiesis to various drugs can be different depending on the species of animal, therefore it is most desirable to test such drugs in a humanized animal model.

Typically, the subject is a mammal. The mammalian subject can be murine, canine, feline, bovine, equine, ovine, primate or human. In one embodiment, the subject is human.

Administration and Dosage

The compositions are administered in any suitable manner, often with pharmaceutically acceptable carriers. Suitable methods of administering treatment in the context of the present invention to a subject are available, and, although more than one route can be used to administer a particular composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective response and/or to alleviate, reduce, cure or at least partially arrest symptoms and/or complications from the disease. An amount adequate to accomplish this is defined as a "therapeutically effective dose."

Routes and frequency of administration of the therapeutic compositions disclosed herein, as well as dosage, will vary from individual to individual as well as with the selected drug, and may be readily established using standard techniques. In general, the pharmaceutical compositions may be administered, by injection (e.g., intracutaneous, intratumoral, intramuscular, intravenous or subcutaneous), intranasally (e.g., by aspiration) or orally. Alternate protocols may be appropriate for individual patients.

As is understood by those skilled in the art, doses can be converted from mg/kg body weight to mg/body surface area, the latter being suitable for use with larger mammalian subjects, including humans. Calculators for allometric scaling are known in the art and readily obtained online. Generally, allometric scaling uses an exponent of 0.75-0.80. For more information, see West & Brown, J Exp Bio 208, 1575-1592, 2005. In addition, the United States Food and Drug Administration publishes "Guidance for Industry: Estimating the Maximum Safe Starting Dose in Initial Clinical Trials for Therapeutics in Adult Healthy Volunteers," which is available from: Office of Training and Communications Division of Drug Information, HFD-240 Center for Drug Evaluation and Research Food and Drug Administration 5600 Fishers Lane Rockville, Md. 20857.

For example, 5 mg/kg 6TG corresponds to a dose of 15.08 mg/m2 for a 20 g mouse. This equals 0.4 mg/kg for a 65 kg human. Absorption after oral 6TG administration is estimated to be 30%, therefore this i.p. dose in mice corresponds to an absorbed dose after oral administration of about 1.3 mg/kg in humans. The conventional oral dose for 6TG single-agent chemotherapy in pediatric patients and adults is 2 mg/kg of body weight per day; if no treatment response is observed after 4 weeks, the dose can be increased to 3 mg/kg.

The method of the invention provides the unexpected advantage of avoiding toxicity subsequent to either excessive irradiation of the subject or excessive 6TG dosage. Surprisingly, effective conditioning and reconstitution of bone marrow can be achieved using less than 105 mg total 6TG dosage over the course of treatment, and over a time course of two to eight weeks. Effective engraftment has been observed with total 6TG dosages of less than 65 mg and in as few as two weeks. In addition, the claimed method allows for the option of monitoring toxicity in an individual subject and adjusting the dosing to optimize effective engraftment with minimal toxicity for each subject. In some embodiments, the subject is administered 1 or 2.5 mg/kg body weight 6TG during the post-engraftment treatments.

Subjects treated in accordance with the method will exhibit over 75% genetically modified hematopoietic cells. In some embodiments, the subject exhibits over 95% genetically modified hematopoietic cells. Successful engraftment can be confirmed in a subject by sampling of the peripheral blood or bone marrow at various intervals after transplantation and chemoselection. The peripheral blood mononuclear cells can be examined by monitoring the levels of HPRT gene disruption, knockdown, or reduction in functional activity, using various standard techniques that are generally familiar to one of ordinary skill in the art, including but not limited to polymerase chain reaction (PCR), quantitative real-time PCR (Q-PCR), surveyor nuclease assay (also referred to as 'Cel-I assay'), Southern blot analysis, Western blot/immunoblot analysis, immunohistochemistry or immunocytochemistry, flow cytometric analysis with intracellular staining, HPRT enzymatic activity analysis, HPLC, mass spectrometry, and the like.

EXAMPLE

The following example is presented to illustrate the present invention and to assist one of ordinary skill in making and using the same. The examples are not intended in any way to otherwise limit the scope of the invention.

Example 1: Combined Preconditioning and In Vivo Chemoselection with 6-Thioguanine Alone Achieves Highly Efficient Reconstitution of Normal Hematopoiesis with HPRT-Deficient Bone Marrow Purine analogs such as 6-thioguanine (6TG) cause myelotoxicity upon conversion into nucleotides by hypoxanthine-guanine phosphoribosyltransferase (HPRT). This example shows the development of a novel and highly efficient strategy employing 6TG as a single agent for both conditioning and in vivo chemoselection of HPRT-deficient HSC. The dose-response and time course of 6TG myelotoxicity were first compared in HPRT-wild type mice and HPRT-deficient transgenic mice. Dosage and schedule parameters were optimized to employ 6TG for myelo-suppressive conditioning, immediately followed by in vivo chemoselection of HPRT-deficient transgenic donor bone marrow (BM) transplanted into syngeneic HPRT-wild type recipients.

At appropriate doses, 6TG induced selective myelotoxicity without any adverse effects on extra-hematopoietic tissues in HPRT-wild type mice, while HSC deficient in HPRT activity were highly resistant to its cytotoxic effects. Combined 6TG conditioning and post transplant chemoselection consistently achieved ~95% engraftment of HPRT-deficient donor BM, with low overall toxicity. Long-term reconstitution of immunophenotypically normal BM was achieved in both primary and secondary recipients. These results provide proof-of-concept that single-agent 6TG can be used both for myelo-suppressive conditioning without requiring irradiation, and for in vivo chemoselection of HPRT-deficient donor cells. The results show that by applying the myelosuppressive effects of 6TG both before (as conditioning) and after transplantation (as chemoselection), highly efficient engraftment of HPRT-deficient hematopoietic stem cells can be achieved.

Clinical efficacy of ex vivo gene therapy using hematopoietic stem cells remains dependent on imparting a selective advantage to the transplanted cells [1, 2]. In order to enhance engraftment and decrease the time needed for lymphohematopoietic reconstitution, in vivo selection strategies employing drug resistance genes such as dihydrofolate reductase (DHFR) [3] or multiple drug-resistance gene 1 (MDR1) [4, 5] have been tested, but have generally failed due to unacceptable toxicity [6] or insufficient selection efficiency [7]. Currently, mutant forms of $O^6$-methylguanine-DNA-methyltransferase (MGM7) are being tested for their ability to confer chemoprotection against BCNU or temozolomide in combination with $O^6$-benzylguanine [8, 9], but these agents also pose a considerable risk of toxicity, and recent observations suggest that mutant MGMT may confer a selective disadvantage when expressed at high levels [10].

Notably, these approaches have generally relied upon transplantation of hematopoietic progenitors over-expressing an exogenous drug resistance gene into recipients preconditioned with myeloablative irradiation; however, chemo-resistance may also be conferred by reduced levels of endogenous enzymes that are normally essential for activation of cytotoxic drugs. In this context, we have previously observed that high levels of the purine nucleotide salvage pathway enzyme hypoxanthine-guanine phosphoribosyltransferase (HPRT) cause increased sensitivity to the purine analog 6-thioguanine (6TG) [11]. The first step of the metabolic conversion of 6TG is catalyzed by HPRT [12], which mediates the addition of ribose 5-phosphate to generate thioguanosine monophosphate (TGMP). Thus, 6TG cytotoxicity is essentially predicated on its HPRT-mediated conversion to thio-dGTPs, which are then incorporated into DNA, inducing futile mismatch repair and subsequent apoptosis.

To confer myeloprotection through reduced activity, the endogenous drug-activating enzyme should normally be highly expressed in hematopoietic progenitors, yet non-essential for normal hematopoiesis. In fact, hematopoietic progenitors normally express high levels of HPRT [13-16], which makes them extremely sensitive to 6TG. Indeed, purine analogs such as 6-mercaptopurine (6MP), azathiopurine (Aza), and 6TG have been used clinically for the treatment of leukemia, particularly in pediatric patients, for half a century [17], as well as for immunosuppression in organ transplant patients, and more recently for autoimmune diseases. At higher doses, myelotoxicity is the most frequent and consistent adverse effect of 6TG when used clinically, and when administered at appropriate concentrations for short periods of time, 6TG is strongly myelosuppressive with little toxicity to other tissues in normal HPRT-wild type animals [11].

In contrast, bone marrow (BM) from HPRT-deficient animals is highly resistant to 6TG [11]. Notably, however, we [11] and others [18] have found that hematopoiesis is phenotypically and functionally normal in Hprt-knockout animals, and although cases of megaloblastic anemia have been associated with hereditary HPRT deficiency (Lesch-Nyhan syndrome) in humans [19], this has been reported to respond well to oral administration of adenine [20]. Furthermore, HPRT deficiency does not appear to be associated with any gross impairment of the immune system in humans or in animals [21].

These observations suggest that HPRT-deficient hematopoietic progenitor cells, which are 6TG-resistant but otherwise normal, should have a selective advantage when transplanted into HPRT-wild type recipients undergoing 6TG treatment, and that this strategy can be used to improve the outcome of ex vivo gene therapy. In fact, Porter and DeGregori [22] previously demonstrated the feasibility of transducing HSC with a lentiviral vector expressing Hprt-targeted shRNA and enriching these engineered hematopoietic cells in vivo by 6TG chemoselection in mice. However, in this previous report, 6TG was employed either at dosages chosen to be only moderately myelosuppressive or only over short periods of selection that were initiated 4 weeks or more following transplantation, and despite preconditioning by total body irradiation, engraftment results were relatively modest and highly variable, ranging from 5-50% [22].

We have now systematically examined the effects of modifying the dose, timing, and duration of 6TG administration on engraftment and hematopoietic reconstitution after transplantation of HPRT-deficient bone marrow. In order to exclude vector transduction efficiency as a variable, we employed BM from Hprt-knockout animals as 'ideal' donor cells, thereby enabling us to focus on the effects of modifying 6TG dosage and scheduling parameters both (i) pre-transplantation for myelosuppressive conditioning of HPRT-wild type recipients, and (ii) post-transplantation for chemoselective amplification of HPRT-deficient donor cell populations. Consequently, here we describe the development of a novel regimen that sequentially employs 6TG as a single agent for both preconditioning and in vivo chemoselection, and show that this combination regimen rapidly and consistently achieves highly efficient engraftment and long-term reconstitution.

Materials and Methods

Mice

Hprt-deficient B6.129P2-Hprt1$^{b-m3}$/J (CD45.2) mice, Hprt-wild type (wt) C57BL/6J, and B6.SJL-Ptprc$^a$Pepc$^b$/BoyJ (CD45.1) mice were originally obtained from the Jackson Laboratory (Bar Harbor, Me.). B6.129P2-Hprt1$^{b-m3}$/J mice carry a 55 kb deletion spanning the promoter and the first 2 exons of the Hprt-gene [23]. Mice were bred and maintained in the institutional specific-pathogen-free animal facility under standard conditions according to institutional guidelines.

6TG Treatment

C57BL/6J and B6.129P2-Hprt1$^{b-m3}$/J mice were injected intraperitoneally (i.p.) with 200 µl of varying doses of 6TG (Sigma-Aldrich, Saint Louis, Mo.) at different time points as described in the figure legends. Control animals were i.p. injected with 200 µl of sterile $H_2O$.

Bone Marrow Transplantation and 6TG In Vivo Chemoselection

Female recipient C57BL/6J (HPRT-wt) or B6.SJL-Ptprc$^a$-Pepc$^b$/BoyJ (HPRT-wt, CD45.1) mice were treated with 10 mg/kg 6TG by i.p. injection 48 hrs before HSCT. For HSCT, 0.8-1×10$^7$ nucleated BM cells isolated from B6.129P2-Hprt1$^{b-m3}$/J male mice (CD45.2) were intravenously injected into HPRT-wt recipients. 6TG (10 mg/kg) was again administered by i.p. injection 2 hrs later, and every 3 days thereafter, at 5 mg/kg for 4 weeks. Serial transplantation into secondary recipient mice was performed using the same cell dose and 6TG preconditioning/chemoselection regimen as above, but using BM from primary recipient mice that had undergone transplantation with 6TG in vivo chemoselection 6 months previously.

Mouse Chromosome X- and Y-Specific Fluorescence In Situ Hybridization

FISH was performed on BM and PBL cells using the mouse-specific Whole Chromosome-Y paint probe/RAB9 (XqF1) DNA probes mix (Kreatech, Amsterdam, Netherlands) according to the manufacturer's protocol. To determine the percentage of male donor HPRT-wt cells in the female recipient C57BL/6J mice, 200 nuclei per slide were counted using a fluorescence microscope (Zeiss) equipped with appropriate dual and triple-colour filters. The following criteria were applied for analyzing FISH: (1) quality of the nuclei was evaluated via DAPI staining, (2) green fluorescent signal for the Y-chromosome was scored, (3) red fluorescent signal for X-chromosome was scored, (4) absence of the green fluorescent signal for the Y-chromosome nucleus was recorded as female, even when only one X-chromosome was detectable (Supplementary FIG. 51; see *Experimental Hematology* 2012, 40:3-13 for supplementary figures).

Immunophenotypic Analysis of Hematopoietic Tissues

After blocking with Mouse BD Fc Block (BD Biosciences, San Jose, Calif.), BM, PBL, thymus, or spleen cells were stained with FITC-, PE-, PerCP- or APC-conjugated rat anti-mouse antibodies against CD45, CD45.2, CD4, CD8, Mac1/Gr1, B220, Sca-1, c-kit, and lineage antibody cocktail. Antibodies were received from Biolegend (San Diego, Calif.) or BD Biosciences. Flow cytometric data were acquired on a BD LSRII running BD FACSDiva (BD Biosciences) and analyzed using FlowJo software (TreeStar, Ashland, Oreg.) (Supplementary Figure S2).

Histopathological Analysis

Necropsy of all mice used in this study and histological examination of all thoracic and abdominal organs and bone marrow was performed by the UCLA Division of Laboratory Animal Medicine Diagnostic Service Laboratory. Tissues were routinely processed or decalcified if necessary, and paraffin sections were cut and stained with hematoxylin and eosin (H&E).

Statistical Analysis

Data were analyzed using the QuickCalcs statistical software program (Graphpad Software Inc.). Unpaired t-tests were used to calculate p values, and p<0.05 was considered statistically significant.

Results

Acute Myelotoxicity of 6TG in HPRT-wt Mice

Figure 1A:
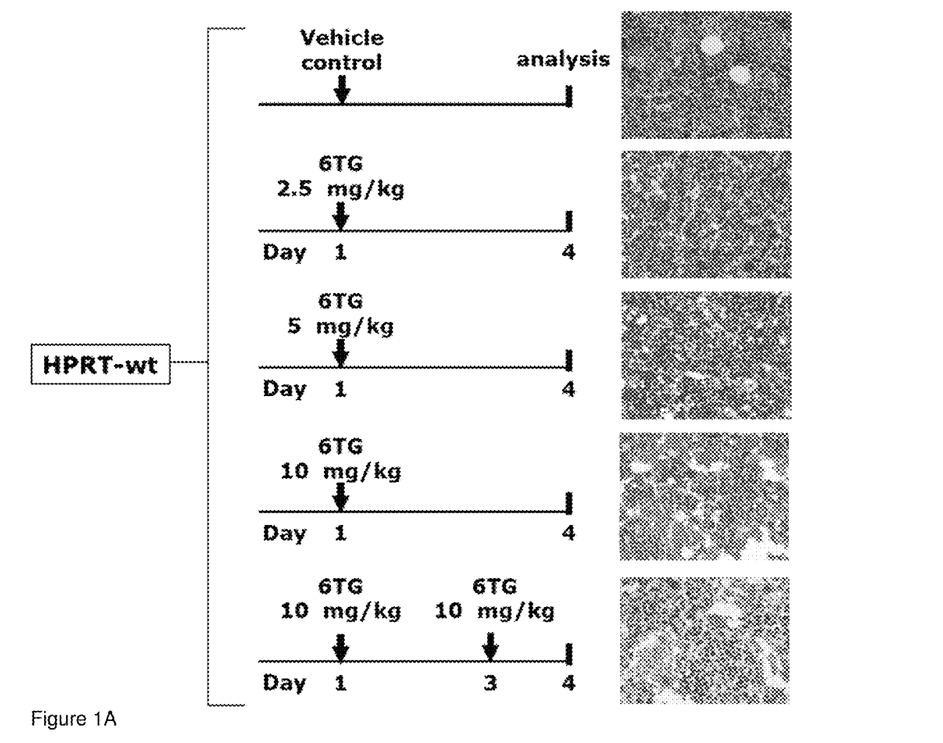
(FIG. 1A) As a dose-finding study, HPRT-wt mice were injected i.p. with vehicle control, or varying 6TG doses ranging from 2.5 to 10 mg/kg, as indicated, on Day 1 (n=3 per group), or with two doses of 10 mg/kg on Day 1 and Day 3 (n=3), respectively. On Day 4 after the first 6TG dose, paraformaldehyde-fixed bone sections were stained with H&E, and BM histology was examined. Representative photomicrographs (40× magnification) are shown for each 6TG conditioning regimen.
Figure 1B:
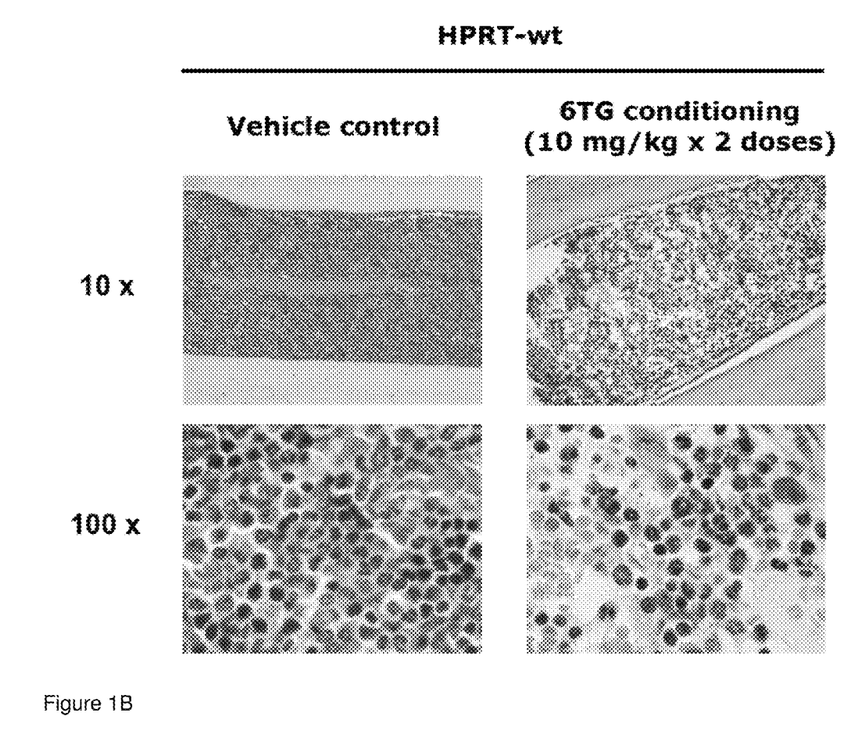
(FIG. 1B) Representative photomicrographs showing overall and detailed BM histology at low (10×) and high (100×) magnification from HPRT-wt mice treated with control vehicle, or with the optimized conditioning regimen consisting of two doses of 10 mg/kg 6TG on Day 1 and Day 3. Histological analyses were performed on Day 4, as above.

The high levels of HPRT expression in hematopoietic progenitors are predicted to mediate a selective myelotoxic effect of 6TG and enable its use as a conditioning regimen. Accordingly, we examined the short-term effects on BM after bolus injections of 6TG at various dosages in HPRT-wt mice. Intraperitoneal injection of a single dose of 2.5 mg/kg, 5.0 mg/kg, or 10 mg/kg 6TG was performed on Day 1, or injection of two doses at 10 mg/kg on Days 1 and 3, and BM histology was examined on Day 4. Increasing myelotoxicity was observed as the total 6TG dosage was increased (FIG. 1A). Vascular structures became progressively prominent and cells of both erythroid and myeloid lineages were depleted. Only vascular endothelium, mesenchymal cells, some mature granulocytes and macrophages, and occasional hematopoietic progenitor cells remained at the highest 6TG dose tested (FIG. 1B).

Figure 2A:
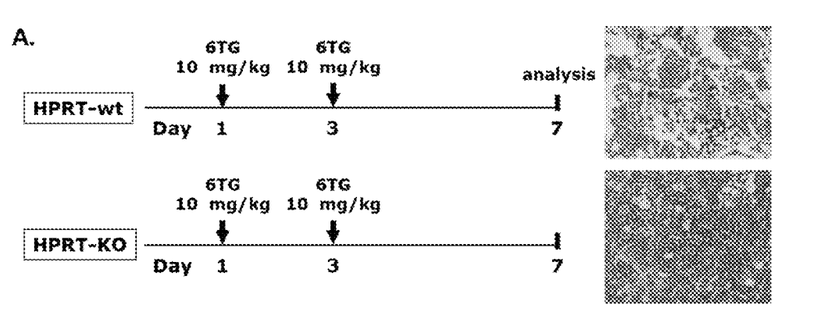

No readily apparent clinical signs were observed on Day 4 with any of the above regimens, but when the observation period was extended, weight loss and pallor of the extremities was seen by Day 7. Histological examination of BM showed severity increasing between Day 4 and Day 7 even without administration of additional doses of 6TG (FIG. 1A, 2A). In concordance with the clinical and histological findings, BM of HPRT-wt mice treated with two doses of 10 mg/kg 6TG and analyzed on Day 7 showed a significant quantitative decrease in the BM nucleated cell count recovered from one femur and tibia ($4.7\times10^6\pm1.0\times10^6$, n=3) compared to that of vehicle control-treated HPRT-wt mice ($1.1\times10^7\pm0.2\times10^7$, n=3) (p<0.01).

Immunophenotypic analysis of the remaining BM hematopoietic cells by flow cytometry (Table 1) revealed that the relative proportion of KLS (lin$^-$/c-kit$^+$/sca-1+) progenitors, which includes HSC with long-term multilineage reconstitution activity [24], significantly decreased 3-fold by Day 4 (p<0.01), and 10-fold by Day 7 (p<0.001) (Table 1-iii, -iv). The relative percentage of mature CD8+ and CD4+ T cells progressively increased over time after 6TG administration, reaching up to 7-fold compared to the controls by Day 7 (p<0.001), likely due to the massively dilated blood vessels and influx of peripheral blood/hemorrhage, as can be also seen in the BM histology. The relative percentage of B220+ cells showed no significant change by Day 4, but had doubled compared to controls by Day 7 after 6TG administration.

TABLE 1

Immunophenotypic analysis of BM hematopoietic cells after 6TG conditioning regimen.

| Cell population | HPRT-wild type | | | | HPRT-deficient |
|---|---|---|---|---|---|
| | i | ii | iii | iv | v |
| CD45$^+$ | 91.5 ± 2.4 | 95.7 ± 0.8 | 95.7 ± 0.1 | 82.8 ± 5.1 | 90.0 ± 2.0 |
| CD4$^+$ | 3.5 ± 0.4 | 11.9 ± 2.5 | 9.6 ± 0.6 | 20.5 ± 3.1 | 2.9 ± 1.7 |
| CD8$^+$ | 3.6 ± 0.1 | 5.3 ± 1.7 | 5.2 ± 0.4 | 25.0 ± 2.7 | 2.7 ± 0.4 |
| B220$^+$ | 28.4 ± 3.3 | 23.1 ± 2.2 | 26.2 ± 1.8 | 56.3 ± 1.5 | 10.7 ± 3.5 |
| Mac1$^+$/Gr1$^+$ | 75.8 ± 1.1 | 85.4 ± 1.8 | 81.0 ± 1.3 | 61.8 ± 3.0 | 79.3 ± 2.9 |
| KLS (HSC) | 4.2 ± 0.6 | 1.3 ± 0.2 | 1.4 ± 0.5 | 0.4 ± 0.2 | 2.0 ± 0.6 |

BM cells were stained with the following rat anti-mouse antibodies: CD45-FITC, CD4-PE, CD8-APC, B220-PerCP, Mac1/Gr1-PE, Sca-1-PE, and c-kit-FITC, and examined by flow cytometry. Treatment and analysis schedules are indicated by small roman numerals, and are the same as in FIG. 1. (i): Vehicle control on Day 1, analysis on Day 4. (ii) Single dose of 10 mg/kg 6TG on Day 1, analysis on Day 4. (iii): Two doses of 10 mg/kg 6TG on Days 1 and 3, analysis on Day 4. (iv) & (v): Two doses of 6TG 10 mg/kg on Days 1 and 3, analysis on Day 7. The last two columns show the results of the same 6TG dosage and schedule (10 mg/kg 6TG × 2 doses) in HPRT-wt (iv) and HPRT-deficient (v) mice, respectively. Percentages of the indicated hematopoietic cell subpopulations are expressed as mean % ± SD of total CD45+ cells (n = 3 per group).

Notably, liver enzymes were not elevated following this conditioning regimen in HPRT-wt mice, indicating the selectivity of 6TG cytotoxicity for hematopoietic progenitors at this dosage, and suggesting its potential for use as a myelosuppressive conditioning regimen.

Lack of Myelotoxicity at 6TG Conditioning Dosage in HPRT-Deficient Mice

In contrast to the above findings, when HPRT-deficient mice were treated with the maximum dosing (two doses of 10 mg/kg 6TG on Days 1 and 3), bone marrow histology remained completely unaffected at day 7 (FIG. 2A), and was comparable to that of the vehicle control group (FIG. 1A). Importantly, the overall count of nucleated BM cells obtained from one femur and tibia of 6TG-treated HPRT-deficient mice ($1.5\times10^7\pm0.3\times10^7$, n=3) was also comparable to that of vehicle control-treated HPRT-wt mice ($1.1\times10^7\pm0.2\times10^7$, n=3), and was significantly higher than in HPRT-wt mice treated with the same 6TG regimen ($4.7\times10^6\pm1.0\times10^6$, n=3) (p<0.005).

Furthermore, the ratios of hematopoietic cell subpopulations in the BM of the 6TG-treated HPRT-deficient mice (Table 1-v) were comparable to those of vehicle control-treated HPRT-wt mice (Table 1-i) and untreated HPRT-wt mice (Table 2, BM % column), as well as untreated HPRT-deficient mice (Table 3, BM % column).

TABLE 2

Immunophenotypic analysis of hematopoietic cells in treatment-naïve HPRT-wt mice.

| Cell population | BM (%) | PBL (%) | Thymus (%) | Spleen (%) |
|---|---|---|---|---|
| CD45$^+$ | 92.6 ± 3.2 | 98.6 ± 0.5 | 98.7 ± 0.6 | 97.1 ± 1.0 |
| CD4$^+$ | 3.9 ± 1.6 | 12.2 ± 2.6 | 6.5 ± 2.1 | 19.7 ± 1.7 |
| CD8$^+$ | 1.6 ± 0.8 | 11.4 ± 1.7 | 3.6 ± 1.2 | 16.5 ± 0.3 |
| CD4$^+$/CD8$^+$ | | | 85.6 ± 4.3 | |
| B220$^+$ | 20.4 ± 8.2 | 47.8 ± 13.2 | | 54.4 ± 4.9 |
| Mac1$^+$/Gr1$^+$ | 87.3 ± 8.1 | 36.1 ± 5.0 | | 18.7 ± 3.9 |
| KLS (HSC) | 3.6 ± 2.4 | | | |

BM, PBL, spleen (S) and thymus (T) were stained with the following rat anti-mouse antibodies: CD45-FITC (BM, PBL, T, S), CD4-PE (BM, PBL, T, S), CD8-APC (BM, PBL, T, S), Mac1/Gr1-PE (BM, PBL, S), B220-PerCP (BM, PBL, S), Sca-1-PE (BM), and c-kit-FITC (BM), and examined by flow cytometry. Percentages of the indicated hematopoietic cell subpopulations are expressed as mean % ± SD of total CD45+ cells (n = 3 per group).

TABLE 3

Immunophenotypic analysis of hematopoietic cells in treatment-naïve HPRT-deficient mice.

| Cell population | BM (%) | PBL (%) | Thymus (%) | Spleen (%) |
|---|---|---|---|---|
| CD45$^+$ | 92.3 ± 1.3 | 96.1 ± 2.7 | 98.7 ± 0.4 | 94.9 ± 1.8 |
| CD4$^+$ | 4.9 ± 1.4 | 15.9 ± 0.8 | 6.5 ± 1.0 | 18.4 ± 2.7 |
| CD8$^+$ | 2.4 ± 0.2 | 11.7 ± 0.7 | 2.9 ± 0.1 | 11.8 ± 1.9 |
| CD4$^+$/CD8$^+$ | | | 86.9 ± 0.9 | |
| B220$^+$ | 28.2 ± 2.7 | 55.7 ± 2.9 | | 51.3 ± 5.5 |
| Mac1$^+$/Gr1$^+$ | 79.7 ± 2.2 | 30.1 ± 4.0 | | 9.9 ± 1.8 |
| KLS (HSC) | 3.3 ± 0.5 | | | |

BM, PBL, spleen (S) and thymus (T) were stained with the following rat anti-mouse antibodies: CD45-FITC (BM, PBL, T, S), CD4-PE (BM, PBL, T, S), CD8-APC (BM, PBL, T, S), Mac1/Gr1-PE (BM, PBL, S), B220-PerCP (BM, PBL, S), Sca-1-PE (BM), and c-kit-FITC (BM), and examined by flow cytometry. Percentages of the indicated hematopoietic cell subpopulations are expressed as mean % ± SD of total CD45+ cells (n = 3 per group).

Taken together, these results suggested that up to two doses of 10 mg/kg 6TG could be employed as an effective conditioning regimen that would be well tolerated for up to 3 days prior to HSCT, with progressively increasing myelotoxicity occurring over a period of 7 days.

Figure 2B:
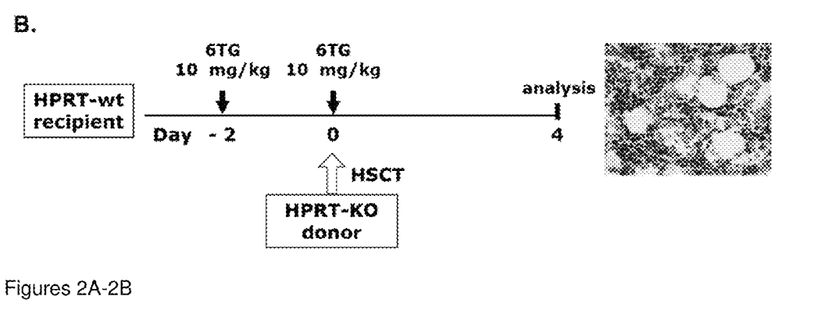
(FIG. 2B) Treatment schedule: HPRT-wt female recipient mice (n=4) received the first conditioning dose of 6TG (10 mg/kg, i.p.) on Day-2, then were transplanted with HPRT-deficient male BM, followed by a second conditioning dose of 6TG (10 mg/kg, i.p.) on Day 0. BM was analyzed on Day 7 after the first 6TG dose. Paraformaldehyde-fixed bone sections stained with H&E (40× magnification) are shown.

Transplantation of HPRT-Deficient BM after 6TG Conditioning in HPRT-Wt Recipients Based on the schedule established above, we employed 6TG (10 mg/kg i.p.) as a conditioning regimen in HPRT-wt recipients (0045.1), with one dose administered 48 hours prior (now designated Day-2, rather than Day 1) and one dose administered on the day of transplantation (designated Day 0, rather than Day 3) per the schedule established above. After conditioning, HPRT-wt recipients were then transplanted with BM from HPRT-deficient congenic donors (CD45.2), At day 4, the marrow showed reduced cellularity with fewer early progenitor cells and increased vascularity (FIG.

2B), and the overall count of nucleated BM cells recovered from these 6TG-conditioned HPRT-wt mice transplanted with HPRT-deficient BM ($3.8\times10^6\pm0.5\times10^6$, n=4) was still significantly reduced (p<0.001) compared to that of the vehicle control-treated HPRT-wt group ($1.1\times10^7\pm0.2\times10^7$, n=3). Flow cytometric analyses of BM showed that at day 4 only 17.8%±4.4% of the total cell population was derived from donor HPRT-deficient CD45.2+ hematopoietic cells.

Threshold for Myelotoxicity after Chronic Low-Dose 6TG Treatment

Figure 3:
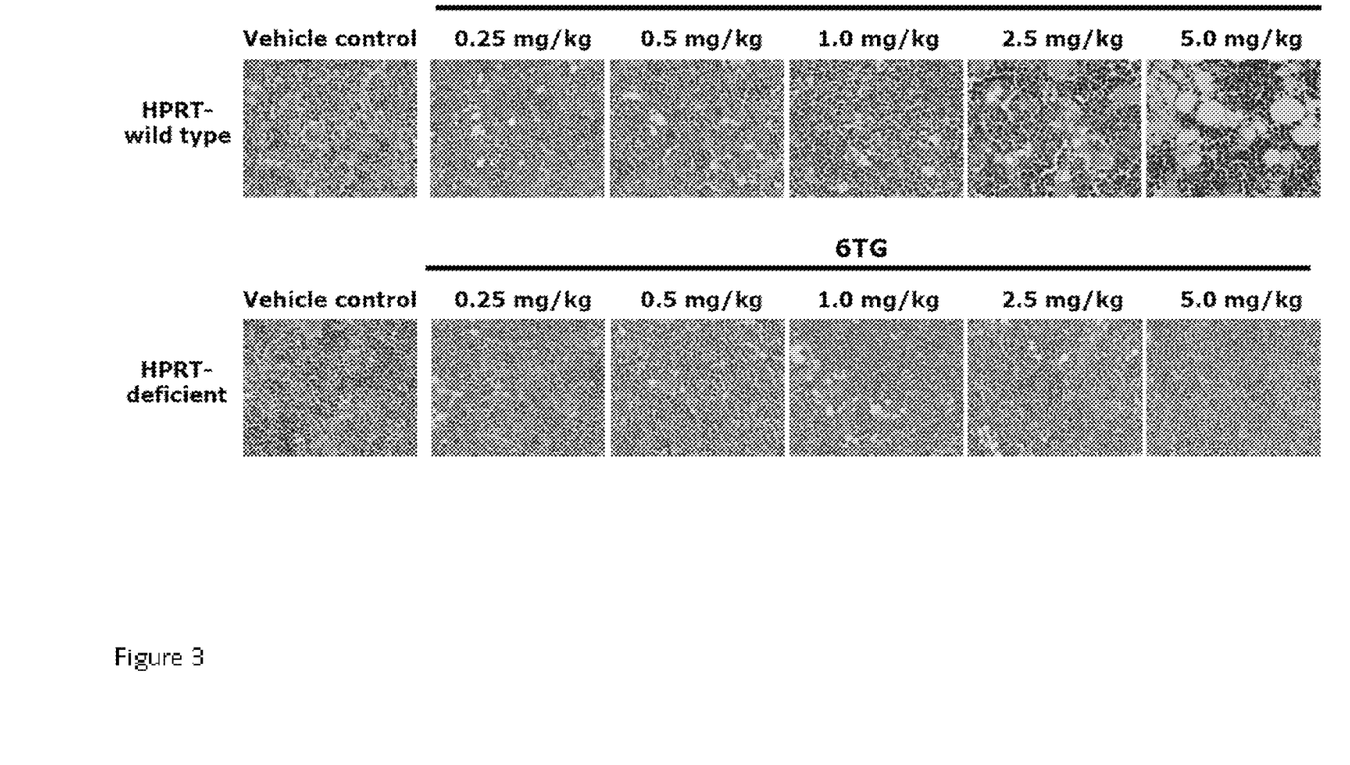
FIG. 3. Dose-response and time course of chronic low-dose 6TG myelotoxicity in HPRT-wt vs. HPRT-deficient mice. HPRT-wild type mice and HPRT-deficient mice were treated every 3 days with different dosages of 6TG or vehicle control (n=3 per group), as shown above each panel. For HPRT-wild type mice, histology was examined at the following time points up to 60 days after initiation of treatment: Vehicle control (Day 60), 6TG 0.25 mg/kg (Day 60), 6TG 0.5 mg/kg (Day 60), 6TG 1.0 mg/kg (Day 38), 6TG 2.5 mg/kg (Day 28), 6TG 5.0 mg/kg (Day 22). For HPRT-deficient mice, histology was examined on Day 60 for all animals. Representative photomicrographs of paraformaldehyde-fixed bone sections stained with H&E (40× original magnification) are shown.

As our results above indicated that 6TG preconditioning alone may not be sufficient to achieve high levels of engraftment, we next performed a dose-finding study in non-transplanted mice given chronic treatment with lower doses of 6TG. HPRT-wt and HPRT-deficient mice (n=3 per group) were injected i.p. with vehicle alone, 0.25 mg/kg, 0.5 mg/kg, 1.0 mg/kg, 2.5 mg/kg, or 5.0 mg/kg 6TG every 3 days for up to 60 days. In HPRT-wt mice, the vehicle control group as well as the 0.25 mg/kg and 0.5 mg/kg 6TG groups showed 100% survival over a period of 60 days, and histological examination of BM in the 0.25 mg/kg and 0.5 mg/kg 6TG groups showed normal cellularity on Day 60 (FIG. 3).

In contrast, in the HPRT-wt 1.0 mg/kg 6TG group, deaths occurred on Day 38 (13 mg/kg total dosage), Day 42 (14 mg/kg total dosage), and Day 51 (17 mg/kg total dosage) (Table S1). At higher dosages, HPRT-wt mice receiving repeated injections of 2.5 mg/kg or 5 mg/kg 6TG consistently showed progressive clinical signs of distress (inactivity, hunched posture, lack of grooming, anorexia), anemia (pallor of extremities) and >10% weight loss, necessitating sacrifice per institutional guidelines on Day 28 (2.5 mg/kg 6TG group; 22.5 mg/kg total dosage) and Day 22 (5.0 mg/kg 6TG group; 35 mg/kg total dosage), respectively. Histological examination of BM from the 1.0 mg/kg 6TG group showed several apoptotic figures and more blast cells than in the lower dosage groups were observed, likely reflecting an initial activation response to the injury (FIG. 3; Day 38). The higher dosage groups also showed significantly reduced cellularity and expansion of vascular structures, with the severity of lesions proportional to the cumulative dosage of 6TG in each group. Mice treated with repeated doses of 2.5 mg/kg 6TG showed reduced cellularity and widespread apoptosis (Day 28). At the highest chronic dosage of 5 mg/kg, BM was markedly depleted, with most of the surviving cells being of myeloid lineage (Day 22).

In contrast to the HPRT-wt mice, all HPRT-deficient mice survived for the duration of the experiment (60 days), independent of the injected 6TG dosage (up to 105 mg/kg maximum total dose, administered according to the same dosing schedules as above) (Table S1). No significant BM pathology was observed in any HPRT-deficient mice, regardless of 6TG dosage, at the terminal time point of the experiment on Day 60 (FIG. 3). No significant treatment-related abnormalities were observed in any other tissues examined, including heart, lung, liver, pancreas, kidney, and spleen. Thus, HPRT-deficient mice showed no toxic effects of chronic 6TG treatment at the 1.0 mg/kg, 2.5 mg/kg, and 5.0 mg/kg doses that caused lethal myelotoxicity in HPRT-wt mice.

Combined 6TG Conditioning and In Vivo Chemoselection Achieves Consistent and Highly Efficient Engraftment of HPRT-Deficient BM Based on the above dose-finding study, we then asked whether 6TG preconditioning combined with continued administration of lower doses of 6TG, beginning immediately after transplantation of HPRT-deficient BM in HPRT-wt recipients, could achieve further chemoselective amplification of engrafted donor cells. Accordingly, female HPRT-wt mice were preconditioned with 6TG (10 mg/kg i.p.), with one dose administered 48 hours prior (Day-2) and one dose administered on the day of transplantation (Day 0) per the conditioning schedule established previously. The HPRT-wt female recipients were then transplanted with HPRT-deficient male BM, and based on the chronic myelotoxicity results above, the recipients were further treated with repeated doses of 2.5 mg/kg 6TG every 3 days for 2 weeks (30 mg/kg total dosage) or 4 weeks (42.5 mg/kg), or repeated doses of 5.0 mg/kg 6TG every 3 days for 2 weeks (40 mg/kg total dosage) or 4 weeks (65 mg/kg total dosage). Analysis was performed immediately after the in vivo chemoselection period at 2 weeks or 4 weeks, respectively (FIG. 4).

As expected, the combined 6TG conditioning, HSCT, and 6TG in vivo chemoselection procedures were well-tolerated, and no signs of distress were observed. In all 6TG-treated groups, 100% of the transplanted animals survived (2 week treatment: n=3 and 4 week treatment: n=8). Body weights decreased initially during the first week after transplantation in the 6TG-treated animals, but stabilized and all animals regained normal weight thereafter. Histopathological analysis showed that overall cellularity and hematopoiesis in the transplanted animals were indistinguishable from the untreated HPRT-wt control, regardless of 6TG chemoselection dosage or duration (FIG. 4).

Chromosome XY-FISH [25, 26] showed that in the groups receiving 2 weeks of 6TG chemoselection, the BM at that time point was already highly reconstituted with donor-derived marrow at levels of 89.3%±1.7 (2.5 mg/kg group) and 95.5%±1.2 (5 mg/kg group). The percentages of donor-derived peripheral blood leukocytes (PBL) at 2 weeks were 13.0%±4.6 (2.5 mg/kg group) and 12.7%±2.9 (5.0 mg/kg group), respectively (Table 4). When in vivo chemoselection was continued for up to 4 weeks after HSCT, the percentage of donor-derived BM cells was again found to be extremely high in both the 2.5 mg/kg group (95.3%±0.9) and the 5.0 mg/kg group (96.7%±1.2). Notably, the percentage of donor-derived PBL was significantly higher in the 5.0 mg/kg group (39.7%±3) in comparison to the 2.5 mg/kg group (29.9%±1.9) at 4 weeks (p<0.005), as well as significantly higher (p<0.0002) than in the groups receiving 2 weeks of chemoselection at either dose (Table 4). Thus, preconditioning with 10 mg/kg 6TG on Day-2 and Day 0, combined with on-going in vivo chemoselection with 5 mg/kg 6TG every 3 days for 4 weeks, yielded maximal levels of BM engraftment by HPRT-deficient donor cells as well as the highest levels of donor-derived PBL; this regimen was employed in further studies.

TABLE 4

Survival and engraftment after combined 6TG conditioning and in vivo chemoselection.

| Treatment | Survival (%) | Engraftment | |
| --- | --- | --- | --- |
| | | BM (%) | PBL (%) |
| 6TG 2.5 mg/kg × 2 weeks | 100 (n = 3) | 89.3 ± 1.7 | 13.0 ± 4.6 |
| 6TG 5.0 mg/kg × 2 weeks | 100 (n = 3) | 95.5 ± 1.2 | 12.7 ± 2.9 |

TABLE 4-continued

Survival and engraftment after combined 6TG conditioning and in vivo chemoselection.

| Treatment | Survival (%) | Engraftment BM (%) | Engraftment PBL (%) |
|---|---|---|---|
| 6TG 2.5 mg/kg × 4 weeks | 100 (n = 3) | 95.3 ± 0.9 | 29.9 ± 1.9 |
| 6TG 5.0 mg/kg × 4 weeks | 100 (n = 8) | 96.7 ± 1.2 | 39.7 ± 3.0 |

Treatment schedules for in vivo chemoselection are as indicated: In vivo chemoselection with 2.5 mg/kg 6TG for 2 weeks, 5.0 mg/kg 6TG for 2 weeks, 2.5 mg/kg 6TG for 4 weeks or 5.0 mg/kg for 4 weeks. All treatment groups showed 100% survival. Engraftment of HPRT-deficient male hematopoietic cells in HPRT-wt female recipient BM and PBL was determined by chromosome XY-FISH (mean % ± SD).

Combined 6TG Conditioning and In Vivo Chemoselection Results in Long-Term Reconstitution of HPRT-Deficient BM The durability of engraftment by HPRT-deficient donor BM using the combined 6TG conditioning and in vivo chemoselection regimen established above was examined 4 months, 7 months, or 12 months after transplantation (i.e., 3 months, 6 months, and 11 months after the end of the 4-week in vivo chemoselection period, respectively). All transplanted animals (4 months: n=8; 7 months: n=6; 12 months: n=5) remained alive and well, showing no signs of any morbidity or discomfort, at all time points examined. Gross pathological and histological examination of these animals revealed no significant abnormalities.

Multi-lineage reconstitution of lymphohematopoiesis by donor-derived progenitor cells was evaluated 4 months after HSCT with combined 6TG preconditioning and in vivo chemoselection, i.e., 3 months after the end of the 4-week chemoselection period. Immunophenotyping of BM, PBL, thymus, and spleen was performed in a congeneic CO45.1/CO45.2 transplant setting using HPRT-deficient CD45.2 mice as donors and HPRT-wt CD45.1 mice as recipients (n=5). All hematopoietic tissues showed high engraftment of CD45.2+ donor cells at levels exceeding 75% of total bone marrow (Table 5). Immunophenotyping of the donor-derived CD45.2+ population showed that the relative percentages of T cells (CD4/CD8), B220+ cells, and macrophages/granulocytes (Mac-1/Gr1) were comparable to those of the treatment-naïve controls (Tables 2 and 3).

TABLE 5

Immunophenotypic analysis of hematopoietic tissues 4 months post-transplantation using 6TG conditioning and in vivo chemoselection regimen in a congeneic CD45.1/CD45.2 transplant model.

| Cell population | BM (%) | PBL (%) | Thymus (%) | Spleen (%) |
|---|---|---|---|---|
| CD45.2+ | 76.1 ± 9.3 | 73.8 ± 5.2 | 89.7 ± 8.3 | 65.9 ± 5.2 |
| CD4+ | 3.2 ± 1.3 | 17.0 ± 3.0 | 10.4 ± 2.8 | 22.6 ± 3.6 |
| CD8+ | 3.0 ± 1.3 | 12.7 ± 0.9 | 4.3 ± 0.8 | 14.9 ± 2.1 |
| CD4+/CD8+ | | | 79.3 ± 4.2 | |
| B220+ | 29.3 ± 6.3 | 45.4 ± 3.8 | | 58.2 ± 8.6 |
| Mac1+/Gr1+ | 80.68 ± 6.1 | 28.2 ± 3.3 | | 14.1 ± 1.6 |

6TG conditioning and in vivo chemoselection was performed as described in text. Recipient BM and PBL were stained with the following rat anti-mouse antibodies: CD45.2-FITC (BM, PBL, T, S), CD4-PE (BM, PBL, T, S), CD8-APC (BM, PBL, T, S), Mac1/Gr1-PE (BM, PBL), B220-PerCP (BM, PBL, S), and examined by flow cytometry. Percentages of the indicated hematopoietic cell subpopulations are expressed as mean % ± SD of total CD45.2+ cells (n = 5 per group).

Figure 5:
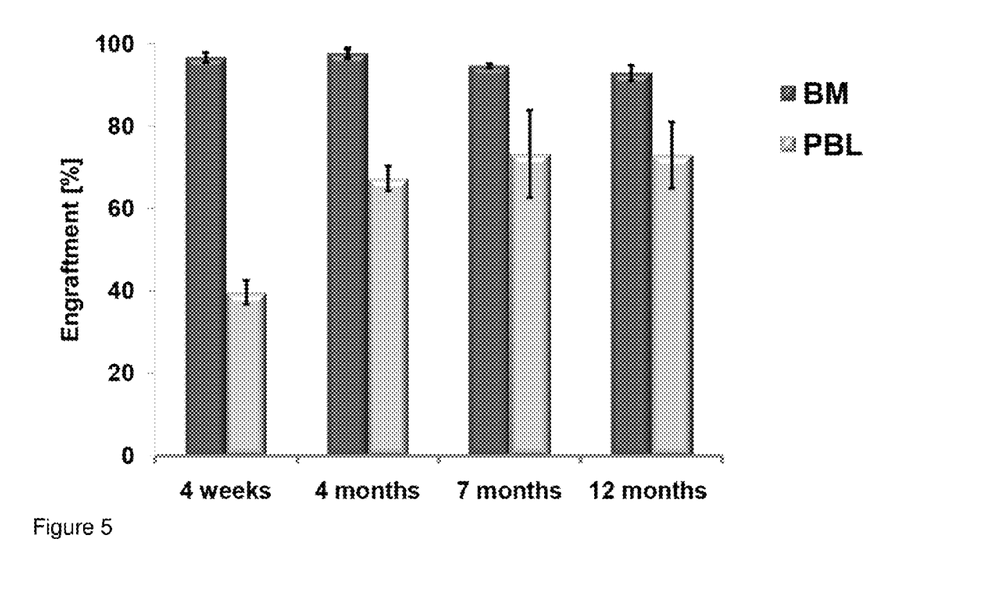
FIG. 5. Long-term hematopoietic reconstitution after transplantation of HPRT-wt recipients with HPRT-deficient donor-derived BM using combined 6TG conditioning and chemoselection. Bar graphs show the percentage of donor-derived cells in bone marrow (BM) and peripheral blood leukocytes (PBL) as determined by XY chromosome FISH analysis at 4 weeks (i.e., immediately after the end of the chemoselection period), and at 4 months, 7 months, and 12 months after transplantation, as indicated.

Engraftment levels were also evaluated by chromosome XY-FISH at the post-transplant 4-month, 7-month, and 12-month time points. Stable long-term reconstitution by donor-derived BM at high levels was observed at all time points, with engraftment levels of 97.7%±0.5% (4 months), 94.7%±1.9% (7 months), and 93.0%±0.8% (12 months), respectively, after transplantation (FIG. 5). Furthermore, the percentage of donor-derived PBL was significantly increased (67.4%±10.6% at 4 months, p=0.01; 73.3%±7.9% at 7 months, p<0.01; 73.0%±10.7% at 12 months, p<0.01) compared to that immediately following the 4-week 6TG selection period (39.7%±3.0%).

The relative percentages of CD4+ and CD8+ cells, B220+ cells, and Mac-1+/Gr1+ cells, as well as KLS (lin$^-$/sca-1$^+$/c-kit$^+$) HSC, were determined in BM by immunophenotyping at 4 months, 7 months, and 12 months (Table 6), and compared to treatment-naïve female HPRT-wt (Table 2) and treatment-naïve male HPRT-deficient (Table 3) control mice. At all three time points, the relative percentage of each cell population was comparable to that in the controls, although KLS cells were elevated at 4 months and 7 months, and within the normal range at 12 months after HSCT. Thus, HPRT-deficient donor-derived marrow was able to achieve long-term reconstitution of normal hematopoiesis for at least 12 months post-transplantation.

TABLE 6

Immunophenotypic analysis of BM at 4 months, 7 months, and 12 months post-transplantation with HPRT-deficient BM using 6TG conditioning and in vivo chemoselection regimen.

| Cell population | 4 months BM (%) | 7 months BM (%) | 12 months BM (%) |
|---|---|---|---|
| CD45+ | 91.6 ± 1.9 | 94.3 ± 2.1 | 82.5 ± 4.9 |
| CD4+ | 2.5 ± 0.6 | 3.8 ± 0.2 | 2.8 ± 2.7 |
| CD8+ | 1.9 ± 0.1 | 2.2 ± 0.4 | 1.8 ± 0.6 |
| B220+ | 51.8 ± 2.4 | 32.9 ± 3.8 | 11.5 ± 2.8 |
| Mac1+/Gr1+ | 77.0 ± 13.0 | 80.8 ± 2.3 | 72.3 ± 5.4 |
| KLS (HSC) | 7.8 ± 1.0 | 7.0 ± 1.1 | 1.8 ± 0.6 |

At the indicated time points after HSCT with 6TG conditioning and in vivo chemoselection, recipient BM cells were stained with the following rat anti-mouse antibodies: CD45-FITC, CD4-PE, CD8-APC, Mac1/Gr1-PE, B220-PerCP, Sca-1-PE, and c-kit-FITC, and examined by flow cytometry. Percentages of the indicated hematopoietic cell subpopulations are expressed as mean % ± SD of total CD45+ cells.

Hematopoietic Reconstitution of Secondary Recipients after Serial Transplantation of HPRT-Deficient Donor BM with Combined 6TG Conditioning and Chemoselection To further evaluate whether the optimized regimen combining 6TG conditioning with chemoselection selects for long-term repopulating HSCs, we next transplanted BM from primary recipients at 7 months post-transplantation into secondary recipients [27] using the same regimen. The secondary transplant recipients were then maintained for 3 months after the end of their 4-week course of 6TG in vivo chemoselection (Supplementary Figure S3). After 6TG conditioning and chemoselection, HPRT-deficient male donor cells that had engrafted primary recipients were able to serially repopulate secondary female recipients at high levels, (95.5%±1.1%, as determined by XY-FISH). Immunophenotypic analysis revealed that the percentages of all cell populations examined in BM and PBL of secondary recipients (Table 7) were again comparable to those of treatment-naïve controls (Tables 2 and 3).

TABLE 7

Immunophenotypic analysis of hematopoietic cells in secondary
recipients after serial transplantation of HPRT-deficient
BM with 6TG conditioning and in vivo chemoselection.

| Cell population | BM (%) | PBL (%) |
| --- | --- | --- |
| CD45+ | 84.6 ± 4.7 | 95.8 ± 1.4 |
| CD4+ | 4.1 ± 1.0 | 7.0 ± 3.3 |
| CD8+ | 2.4 ± 0.8 | 7.0 ± 3.2 |
| B220+ | 19.1 ± 2.9 | 33.3 ± 12.3 |
| Mac1+/Gr1+ | 78.3 ± 4.7 | 31.6 ± 11.7 |

Serial transplantation with 6TG conditioning and in vivo chemoselection regimen was performed as described in FIG. S3. Secondary recipient BM and PBL were stained with the following rat anti-mouse antibodies: CD45-FITC (BM, PBL), CD4-PE (BM, PBL), CD8-APC (BM, PBL), Mac1/Gr1-PE (BM, PBL), and B220-PerCP (BM, PBL), and examined by flow cytometry. Percentages of the indicated hematopoietic cell subpopulations are expressed as mean % ± SD of total CD45+ cells (n = 6 per group).

We have developed an optimized regimen that employs 6TG as a single agent for pre-transplant conditioning as well as continued post transplant in vivo chemoselection of HPRT-deficient donor HSC. This combined 6TG conditioning and chemoselection strategy achieved efficient HSC engraftment with low overall toxicity, through a progressive and simultaneous replacement process, in which recipient hosts showed little if any distress and 100% survival, while their BM was rapidly and almost completely replaced by HPRT-deficient donor cells, consistently achieving ~95% engraftment by XY-FISH, and >75% by CD45.2 immunophenotyping. The percentage of donor-derived PBL increased significantly over time (4 and 7 months post-transplantation) compared to that immediately following the 4-week 6TG selection period. Residual recipient cells in PBL likely reflect a lower turnover of non-dividing mature cells in PBL. Stable long-term reconstitution of the BM was achieved in both primary and secondary recipients. Immunophenotyping analysis of BM, PBL, spleen, and thymus showed that, after long-term reconstitution, hematopoietic differentiation was unaffected by 6TG in vivo chemoselection.

These results also confirm our previous observation that, at appropriate concentrations, 6TG appears to induce selective myelotoxicity without any adverse effects on extra-hematopoietic tissues. HPRT is expressed at low levels in all somatic cells [30], and inherited loss of HPRT gives rise to Lesch-Nyhan syndrome [31] which manifests as severe mental retardation and behavioral abnormalities, as higher levels of HPRT expression and activity have been found in the central nervous system, particularly during neural development [32]. However, since fully differentiated neurons do not undergo replication, these higher levels do not translate into higher 6TG neurotoxicity in mature adults.

In previous work by Porter and DeGregori [22], total body irradiation of 4.5 Gy was used to achieve myeloablation, and 6TG was employed only for chemoselection at later time periods. In contrast, in our regimen, 6TG as a single agent fulfills the dual role of conditioning (cytoreduction of host BM) and chemoselective drug (amplification of donor BM). It is known that 6TG toxicity requires two rounds of DNA replication to result in apoptosis [33] and therefore shows a delayed effect. Our results also indicated a dose- and time-dependent myelotoxic effect of 6TG. Thus, conditioning with 10 mg/kg 6TG prior to transplantation may improve the outcome of 6TG in vivo chemoselection by compensating for the delay in 6TG myelotoxicity and providing an adequate niche for HSC at the time of transplantation.

In addition, Porter et al. employed 6TG at much lower doses ranging from 0.25-2 mg/kg over short periods of time, starting more than a month after transplantation, resulting in variable engraftment levels ranging from 5-50%. In our current study, we have confirmed that mice transplanted with Hprt-deficient BM can tolerate 6TG doses 5- to 40-fold higher, with administration of the chemoselective drug started immediately post-transplant, and continued over considerably longer selection periods.

In order to translate the use of the 6TG in vivo chemoselection strategy into a clinically feasible approach, it is necessary to develop methods to genetically engineer normal HSC to render them HPRT-deficient and thus 6TG-resistant. Furthermore, it should be emphasized that our current study was limited to employing this strategy for bone marrow transplantation in syngeneic mice, which models the situation in the autologous transplant setting. Whether this strategy will be equally useful in the allogeneic setting remains to be seen, as reduced-intensity conditioning regimens are being used routinely to circumvent the toxicity of traditional myeloablative regimens. Potential issues that may need to be addressed include the possibility of spontaneous 6TG resistance arising in leukemic cells after allogeneic transplantation for hematopoietic malignancies, and possible exacerbation of graft-vs.-host disease when allogeneic donor cells are selectively amplified in vivo.

REFERENCES

[1] Biffi A, Cesani M. Curr Gene Ther. 2008; 8:135-146.
[2] Persons D A, Nienhuis A W. Curr Opin Mol Ther. 2002; 4:491-498.
[3] Williams D A, Hsieh K, DeSilva A, Mulligan R C. J Exp Med. 1987; 166:210-218.
[4] Mickisch G H, Aksentijevich I, Schoenlein P V, et al. Blood. 1992; 79:1087-1093.
[5] Sorrentino B P, Brandt S J, Bodine D, et al. Science. 1992; 257:99-103.
[6] Zaboikin M, Srinivasakumar N, Schuening F. Cancer Gene Ther. 2006; 13:335-345.
[7] Southgate T, Fairbairn L J. Expert Rev Mol Med. 2004; 6:1-24.
[8] Milsom M D, Williams D A. DNA Repair (Amst). 2007; 6:1210-1221.
[9] Neff T, Beard B C, Kiem H P. Blood. 2006; 107:1751-1760.
[10] Schambach A, Baum C. DNA Repair (Amst). 2007; 6:1187-1196.
[11] Aubrecht J, Goad M E, Schiestl R H. J Pharmacol Exp Ther. 1997; 282:1102-1108.
[12] Stout J T, Caskey C T. Annu Rev Genet. 1985; 19:127-148.
[13] Fontenelle L J, Henderson J F. Biochim Biophys Acta. 1969; 177:175-176.
[14] Holmsen H, Rozenberg M C. Biochim Biophys Acta. 1968; 157:266-279.
[15] Lajtha L G, Vane J R. Nature. 1958; 182:191-192.
[16] Lowy B A, Ramot B, London I M. J Biol Chem. 1960; 235:2920-2923.
[17] Elion G B. Science. 1989; 244:41-47.
[18] Ansell J D, Samuel K, Whittingham D G, et al. Development. 1991; 112:489-498.
[19] Torres R J, Puig J G. Orphanet J Rare Dis. 2007; 2:48.
[20] van der Zee S P, Schretlen E D, Monnens L A. Lancet. 1968; 1:1427.
[21] Seegmiller J E, et al. Adv Exp Med Biol. 1977; 76A:412-433.
[22] Porter C C, DeGregori J. Blood. 2008; 112:4466-4474.
[23] Hooper M, Hardy K, Handyside A, Hunter S, Monk M. Nature. 1987; 326:292-295.

[24] Bryder D, Rossi D J, Weissman I L. Am J Pathol. 2006; 169:338-346.
[25] Rondon G, Giralt S, Pereira M, et al. Leuk Lymphoma. 1997; 25:463-467.
[26] Brazelton T R, Blau H M. Stem Cells. 2005; 23:1251-1265.
[27] Krause D S, Theise N D, Collector M I, et al. Cell. 2001; 105:369-377.
[28] Olsen N J, Kovacs W J. Immunol Res. 2001; 23:281-288.
[29] Olsen N J, Gu X, Kovacs W J. J Clin Invest. 2001; 108:1697-1704.
[30] Kelley W N, Wyngaarden, J. B. In: J. B. Stanbury J B W, et al., ed. The Metabolic Basis of Inherited Disease, 5th ed. New York: McGraw Hill; 1983. p. 1115-1143.
[31] Lesch M, Nyhan W L. Am J Med. 1964; 36:561-570.
[32] Lo Y F, Palmour R M. Biochem Genet. 1979; 17:737-746.
[33] Mojas N, Lopes M, Jiricny J. Genes Dev. 2007; 21:3342-3355.
[34] An D S, Qin F X, Auyeung V C, et al. Mol Ther. 2006; 14:494-504.
[35] Grimm D, Streetz K L, Jopling C L, et al. Nature. 2006; 441:537-541.

Example 2: Creation of HPRT-Deficient Cells

This example is directed at translational application to ex vivo gene therapy in the autologous setting, employing both third-generation lentiviral vectors expressing different HPRT-targeted shRNA candidate sequences, as well as nucleofection of zinc finger nucleases (ZFN) targeting HPRT. The latter approach is advantageous as only transient expression of the ZFN construct is needed to achieve permanent knockout of the target gene, thereby mitigating the potential for insertional mutagenesis as a result of the genetic engineering procedure. In this context, this strategy is unique in imparting a selective advantage to transplanted cells through an enzyme deficiency, rather than inserting a new transgene to achieve chemoresistance. HPRT-targeted shRNA was successful in down-regulating HPRT to undetectable levels. In addition, HPRT has been successfully knocked out using ZFN.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method of radiation-free hematopoietic stem cell (HSC) transplantation, the method comprising:
   (a) administering to a mammalian subject one or two doses of 2 to 10 mg/kg body weight of a purine base analog selected from 6-thioguanine (6TG), 6-mercaptopurine (6-MP), or azathiopurine (AZA), as a pre-conditioning step;
   (b) engrafting into the subject hypoxanthine-guanine phosphoribosyltransferase (HPRT)-deficient donor HSCs within 48 to 72 hours of the pre-conditioning step; and
   (c) immediately administering to the subject about 1 to 5 mg/kg of the purine base analog every two to four days for two to eight weeks without allowing for a recovery period;
   wherein the method is performed in the absence of pre-conditioning via radiation, and wherein the subject is suspected of having or has a disease or disorder.

2. The method of claim 1, wherein the subject is human.

3. The method of claim 1, wherein the subject has a hereditary or genetic disorder.

4. The method of claim 1, wherein the subject has an acquired disease affecting lymphohematopoietic cells.

5. The method of claim 4, wherein the disease or disorder is human immunodeficiency virus (HIV) infection or acquired immune deficiency syndrome (AIDS).

6. The method of claim 4, wherein the disease or disorder is a lymphohematopoietic malignancy.

7. The method of claim 1, wherein the disease or disorder is of hematopoietic or thrombopoietic or lymphopoietic system.

8. The method of claim 7, wherein the disease or disorder of the hematopoietic system is a hemoglobinopathy.

9. The method of claim 1, wherein the method further comprises bone marrow transplantation.

10. The method of claim 1, wherein the purine base analog is 6TG.

11. The method of claim 1, wherein the total 6TG dosage administered to the subject in the administering of steps (a) and (c) does not exceed 105 mg.

12. The method of claim 1, wherein the total 6TG dosage administered to the subject in the administering of steps (a) and (c) does not exceed 75 mg.

13. The method of claim 1, wherein the administering of step (c) is performed every 3 days and for not more than four weeks following the engrafting step.

14. The method of claim 1, wherein no more than 5 days elapse between administering dosages of purine base analog throughout steps (a) to and (c).

15. The method of claim 1, wherein the subject exhibits over 75% genetically modified hematopoietic cells.

16. The method of claim 1, wherein the subject exhibits over 95% genetically modified hematopoietic cells.

17. The method of claim 1, wherein the HPRT-deficient HSCs to be transplanted have been rendered HPRT-deficient via introduction of sequences encoding zinc finger nucleases (ZFNs), transcriptional activator-like effector nucleases (TALENs), small fragment homologous recombination (SFHR) template strands, inhibitory RNAs (siRNAs) or microRNAs (miRNAs), antisense RNAs, trans-splicing RNAs, ribozymes, intracellular antibodies, or dominant-negative or competitive inhibitor proteins.

18. The method of claim 1, wherein the HPRT-deficient HSCs to be transplanted have been rendered HPRT-deficient via introduction of sequences encoding zinc finger nucleases (ZFNs).

19. The method of claim 1, wherein the HPRT-deficient HSCs to be transplanted have been rendered HPRT-deficient via introduction of sequences encoding transcriptional activator-like effector nucleases (TALENs).

20. The method of claim 1, wherein the HPRT-deficient HSCs to be transplanted have been rendered HPRT-deficient via introduction of sequences encoding inhibitory RNAs (siRNAs).

21. The method of claim 1, wherein the HPRT-deficient HSCs to be transplanted have been genetically modified.

22. The method of claim 1, wherein the transplanted HSCs are autologous or syngeneic.

23. The method of claim 1, wherein the transplanted HSCs are allogeneic.

24. The method of claim 1, wherein the subject is not treated with myeloablative radiation.

25. A method of treating symptoms of a disease or disorder affecting lymphohematopoietic cells in a subject, the method comprising:
- (a) administering to the subject one or two doses of 2 to 10 mg/kg body weight of a purine base analog selected from 6-thioguanine (6TG), 6-mercaptopurine (6-MP), or azathiopurine (AZA), as a pre-conditioning step;
- (b) engrafting into the subject hypoxanthine-guanine phosphoribosyltransferase (HPRT)-deficient donor HSCs within 48 to 72 hours of the pre-conditioning step; and
- (c) immediately administering to the subject about 1 to 5 mg/kg of the purine base analog every two to four days for two to eight weeks without allowing for a recovery period;

wherein the method is performed in the absence of pre-conditioning via radiation.

26. The method of claim 25, wherein the disease or disorder is human immunodeficiency virus (HIV) infection or acquired immune deficiency syndrome (AIDS).

27. The method of claim 25, wherein the disease or disorder is a lymphohematopoietic malignancy.

28. The method of claim 25, wherein the disease or disorder is of hematopoietic or thrombopoietic or lymphopoietic system.

29. The method of claim 28, wherein the disease or disorder of the hematopoietic system is a hemoglobinopathy.

30. The method of claim 25, wherein the method further comprises bone marrow or hematopoietic stem cell transplantation.

31. The method of claim 25, wherein the subject is human.

32. The method of claim 25, wherein the purine base analog is 6TG.

33. The method of claim 25, wherein the administering of step (c) is performed every 3 days and for not more than four weeks following the engrafting step.

34. The method of claim 25, wherein no more than 5 days elapse between administering dosages of purine base analog throughout steps (a) to and (c).

35. The method of claim 25, wherein the subject exhibits over 75% genetically modified hematopoietic cells.

36. The method of claim 25, wherein the subject exhibits over 95% genetically modified hematopoietic cells.

37. The method of claim 25, wherein the HPRT-deficient HSCs to be transplanted have been rendered HPRT-deficient via introduction of sequences encoding zinc finger nucleases (ZFNs), transcriptional activator-like effector nucleases (TALENs), small fragment homologous recombination (SFHR) template strands, inhibitory RNAs (siRNAs) or microRNAs (miRNAs), antisense RNAs, trans-splicing RNAs, ribozymes, intracellular antibodies, or dominant-negative or competitive inhibitor proteins.

38. The method of claim 25, wherein the HPRT-deficient HSCs to be transplanted have been rendered HPRT-deficient via introduction of sequences encoding zinc finger nucleases (ZFNs).

39. The method of claim 25, wherein the HPRT-deficient HSCs to be transplanted have been rendered HPRT-deficient via introduction of sequences encoding transcriptional activator-like effector nucleases (TALENs).

40. The method of claim 25, wherein the HPRT-deficient HSCs to be transplanted have been rendered HPRT-deficient via introduction of sequences encoding inhibitory RNAs (siRNAs).

41. The method of claim 25, wherein the HPRT-deficient HSCs to be transplanted have been genetically modified.

42. The method of claim 25, wherein the transplanted HSCs are autologous or syngeneic.

43. The method of claim 25, wherein the transplanted HSCs are allogeneic.

44. The method of claim 25, wherein the subject is not treated with myeloablative radiation.

* * * * *